United States Patent [19]
Klinkhammer

[11] Patent Number: 5,380,069
[45] Date of Patent: Jan. 10, 1995

[54] PLEATED PANEL STRIP BRUSH CONSTRUCTION

[76] Inventor: Ronald W. Klinkhammer, One Renton Pl., 555 S. Renton Village Pl., Renton, Wash. 98055-3225

[21] Appl. No.: 869,233

[22] Filed: Apr. 14, 1992

Related U.S. Application Data

[63] Continuation-in-part of Ser. No. 664,487, Mar. 4, 1991, which is a continuation-in-part of Ser. No. 145,771, Jan. 19, 1988.

[51] Int. Cl.$^6$ .................................................. A46B 9/04
[52] U.S. Cl. ...................................... 300/21; 15/167.1
[58] Field of Search ............... 15/106, 167.1, 167.2; 300/21

[56] References Cited
U.S. PATENT DOCUMENTS

| | | |
|---|---|---|
| 1,097,122 | 5/1914 | Engstrom . |
| 2,171,591 | 9/1939 | Minich .................. 15/167.1 X |
| 2,265,102 | 12/1941 | Cressler et al. ............... 15/167.1 |
| 3,551,936 | 1/1971 | Kutik et al. .................... 15/187 |
| 4,366,592 | 1/1983 | Bromboz ........................ 15/22 R |
| 4,646,381 | 3/1987 | Weihrauch .................... 15/167 R |
| 4,691,405 | 9/1987 | Reed .................................. 15/201 |
| 5,011,230 | 4/1991 | Weihrauch ....................... 300/21 |

*Primary Examiner*—Douglas D. Watts
*Attorney, Agent, or Firm*—Wells, St. John, Roberts, Gregory & Matkin

[57] ABSTRACT

Brushes are shown in preferred forms which have a series of bristle panels mounted upon a shaft. Each bristle panel has a plurality of bristles. The bristle panels are preferably formed by integrally molding a concatenated series connected by flexible webs. The series is pleated and mounted upon the shaft. An anchor is connected to keep the bristle panels upon the shaft. The bristle panels can be provided with various bristle configurations to vary the brushing action. This construction allows sterilization of the brush and components using economical ultraviolet sterilization techniques.

30 Claims, 4 Drawing Sheets

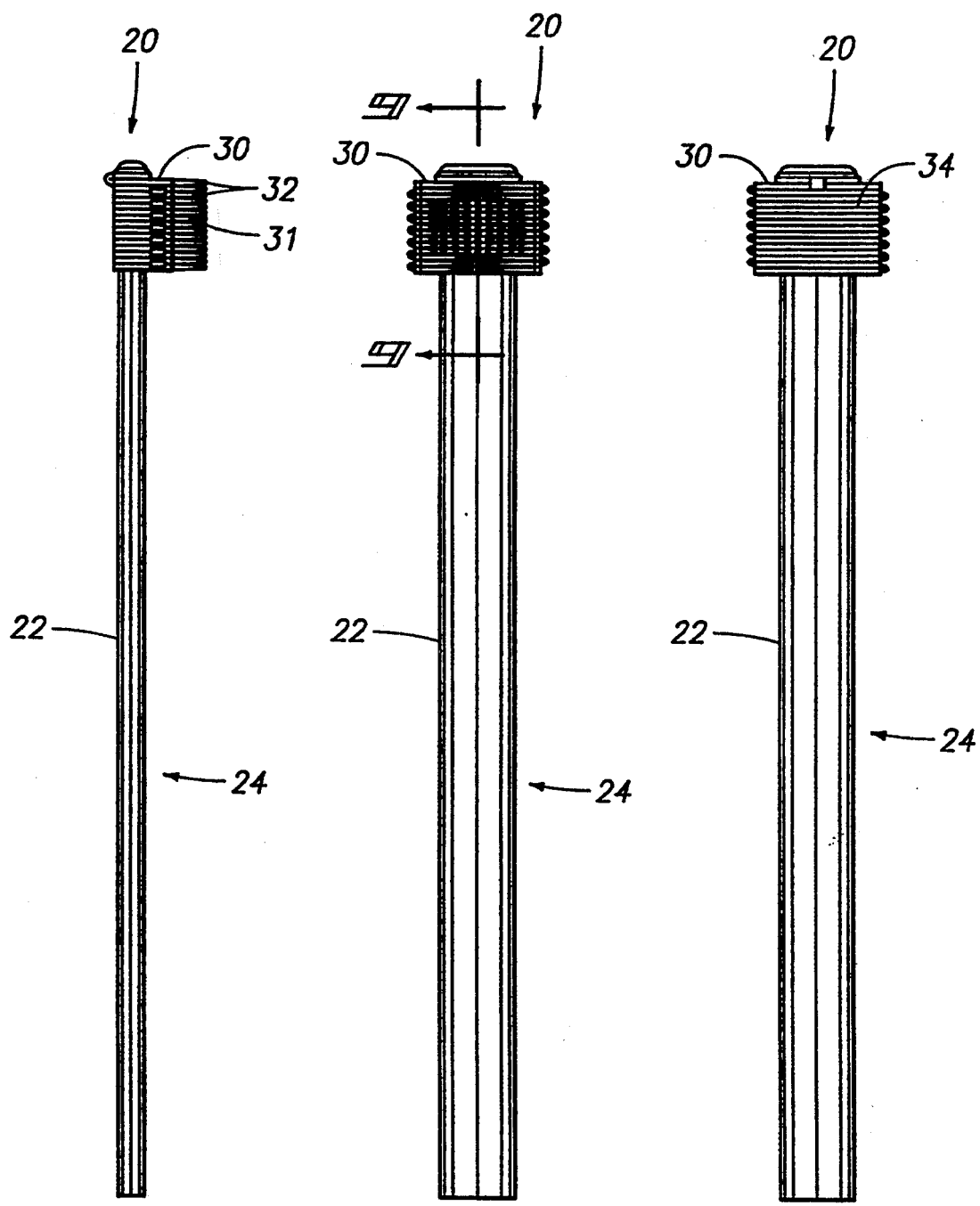

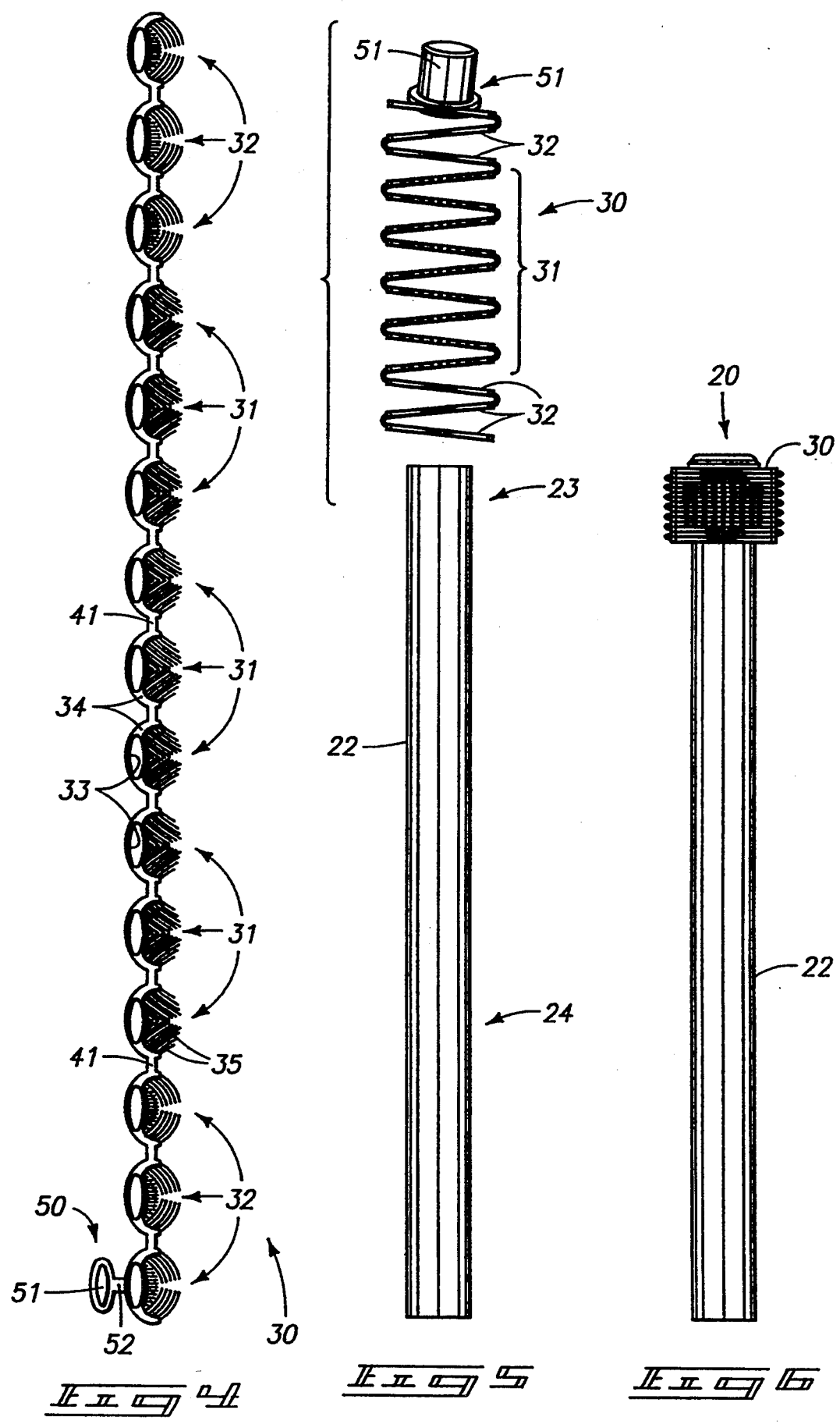

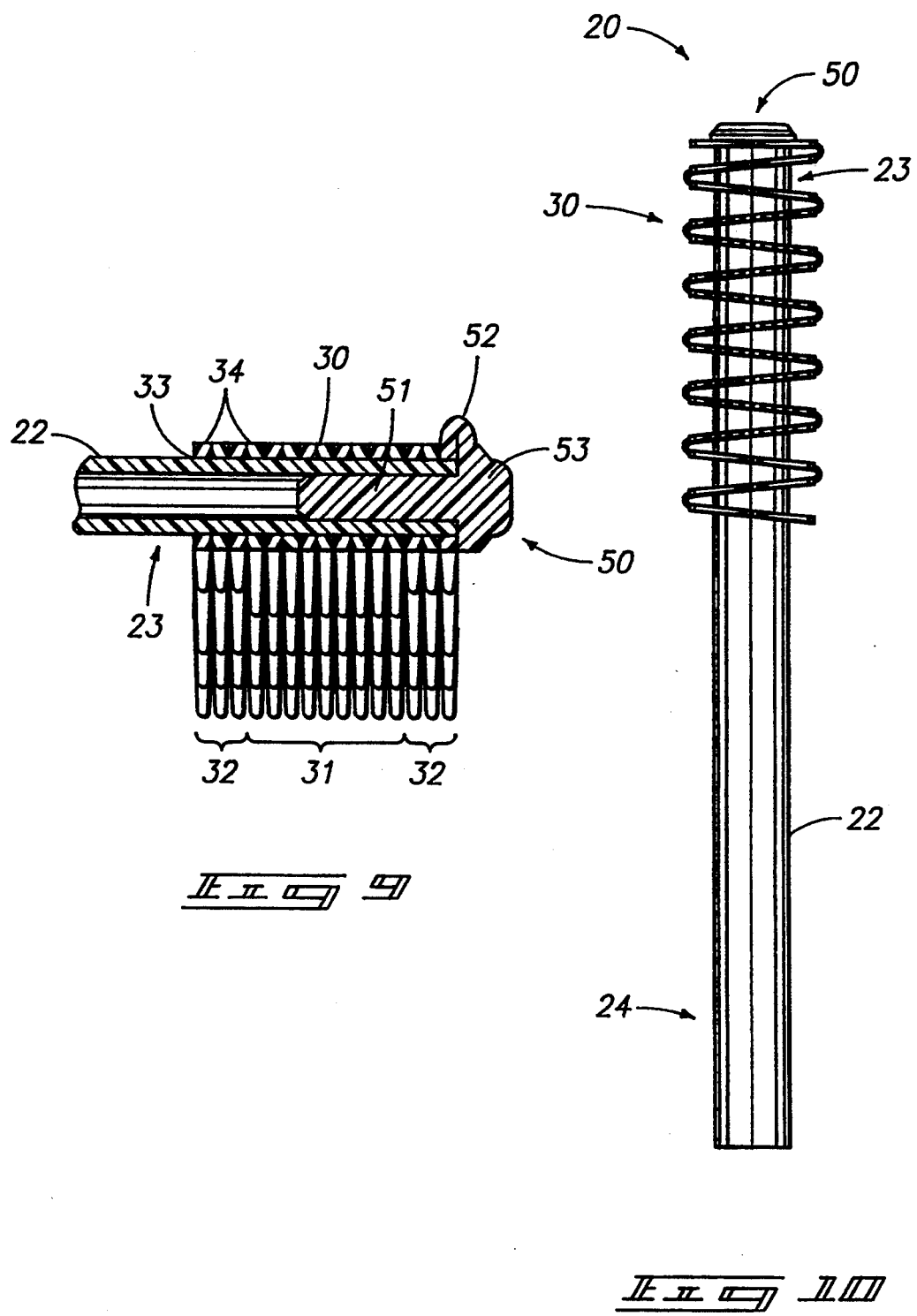

PLEATED PANEL STRIP BRUSH CONSTRUCTION

CROSS-REFERENCE TO RELATED APPLICATIONS

This is a continuation-in-part of co-pending U.S. patent application Ser. No. 664,487 filed Mar. 4, 1991; which was a continuation-in-part of U.S. patent application Ser. No. 145,771 filed Jan. 19, 1988. Priority is claimed upon such prior applications as allowed by law.

TECHNICAL FIELD

The technical field of this invention is the design and construction of brushes, particularly toothbrushes.

BACKGROUND OF THE INVENTION

Toothbrushes are used by most people for a limited period of time, typically in the range of one month to less than one year. Because of their widespread use and frequent replacement, the market in toothbrushes is very large.

In the United States and other countries it is common for dental professionals to give complementary toothbrushes to patients at the time of routine dental examinations, teeth cleaning or other dental procedures. Toothbrush manufactures utilize complementary toothbrushes as an opportunity to introduce new products or introduce their product to additional consumers. However, the cost of supplying free toothbrushes is substantial and any reduction of the costs of manufacture is of significance to the toothbrush manufacturer. Alternatively, if the dental professional is paying for the complementary toothbrushes then there is a continuous desire to reduce this cost.

The large volume of toothbrushes produced every year also indicates the economic significance of any invention which can produce significant savings in the costs of production. Accordingly, there is a continuing interest in producing less costly toothbrushes.

The need for greater economy in the production of toothbrushes is of particular concern for toothbrushes which provide compound brush fields. Compound brush fields utilize several brush segments or fields which are supported is a manner which allows differing action. Such compound brush fields are advantageous in providing combined brushing of the top and sides of teeth in a single pass. However, such compound field toothbrushes are relatively more expensive to construct and therefore are in particular need of greater economy of production.

Health considerations are also significant in the production and distribution of toothbrushes. Prior to this time it has been effectively impossible to economically present sterilized toothbrushes for sale. Accordingly, toothbrushes sold before now are not sterile. This difficulty exists because inexpensive sterilization involves beaming bacteriocidal rays, such as ultraviolet light, onto the surfaces being sterilized. However, this inexpensive sterilization technique cannot be used with prior toothbrush designs because the interstices between the bristles receive only an attenuated intensity of the ultraviolet beam and sterilization cannot be assured. Autoclaving is an alternative sterilization procedure which can be used to produce a sterile toothbrush. Unfortunately, the cost of processing toothbrushes through an autoclave is too high to be practical.

The current invention includes a novel toothbrush construction which is easy and economical to produce and provides compound brushing fields. Of equal significance it provides a design which can be manufactured and sterilized using economical ultraviolet sterilization techniques. It also includes novel methods for constructing such a toothbrush. Other advantages and benefits of the invention are indicated or apparent from the description of the invention given herein.

BRIEF DESCRIPTION OF THE DRAWINGS

One or more preferred forms of the invention are described herein with reference to the accompanying drawings. The drawings are briefly described below.

FIG. 1 is a left side view of a preferred toothbrush according to this invention. The right side view is a mirror image of FIG. 1.

FIG. 2 is a front view of the toothbrush of FIG. 1.

FIG. 3 is a rear view of the toothbrush of FIG. 1.

FIG. 4 is a plan view showing a preferred bristle assembly strip array used as a component in the toothbrush shown in FIG. 1.

FIG. 5 is a diagrammatic front view illustrating components used in a preferred method for constructing the toothbrush of FIG. 1.

FIG. 6 is a diagrammatic front view further illustrating the preferred method of construction illustrated in FIG. 5, with the toothbrush in a fully assembled condition.

FIG. 9 is a partial longitudinal sectional view of the head portion of the toothbrush of FIG. 1.

FIG. 10 is a front view showing the toothbrush of FIG. 1 in a further mode of operation which allows easier cleaning of the brush head.

DETAILED DESCRIPTION OF THE PREFERRED EMBODIMENTS

Figure 7:
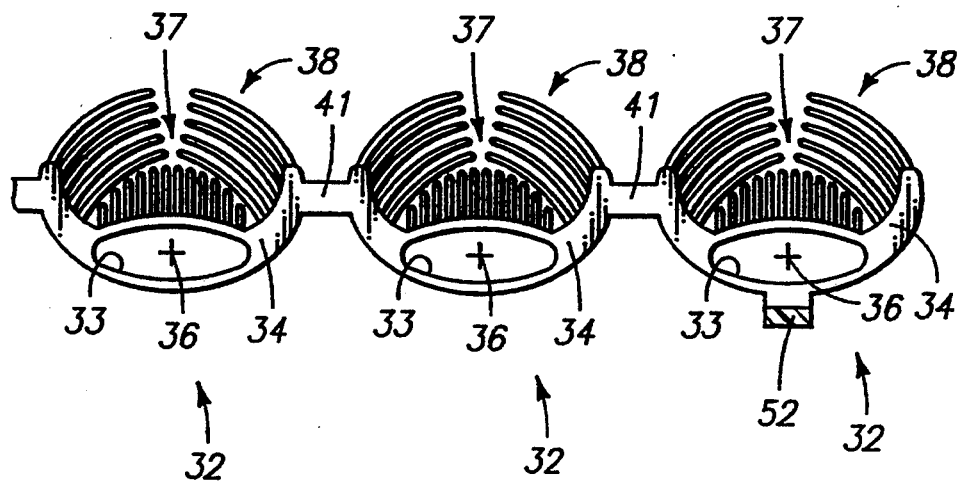
FIG. 7 is an enlarged view of part of the strip shown in FIG. 4.
Figure 8:
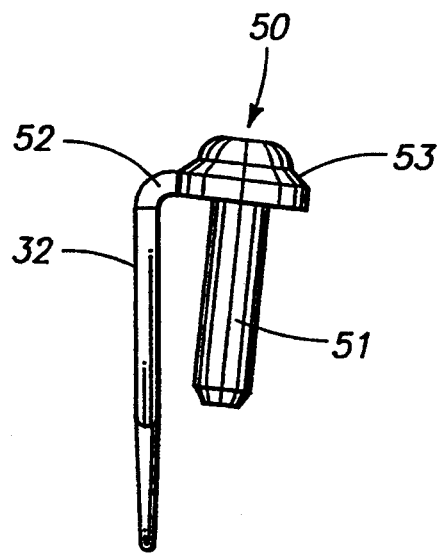
FIG. 8 is an enlarged view of part of the strip shown in FIG. 4 in an alternative orientation.

This disclosure of the invention is submitted in furtherance of the constitutional purposes of the U.S. Patent Laws "to promote the progress of science and useful arts" (Article 1, Section 8).

FIGS. 1–3 show the overall appearance of a preferred toothbrush 20 constructed according to this invention. Toothbrush 20 includes a shaft 22 and a bristle assembly 30. As shown, shaft 22 is a rod shaped member having an outer surface which is advantageously oval or elliptical in cross-section. Shaft 22 is most preferably a hollow tubular member having a shape and size which is consistent over its length. This preferred form allows the shaft to be easily and inexpensively produced from extruded plastic tubing cut to the desired length. The plastic or other material used for the shaft can be selected from a variety of suitable materials.

FIG. 5 shows the bristle assembly 30 in an exploded arrangement away from shaft 24. The shaft has a head portion 23 which underlies the bristle assembly when installed, and a handle portion 24 which can be easily grasped as a handle of the toothbrush 20. FIG. 5 also shows the bristle assembly in a pleated formation. The bristle assembly 30 is installed upon the shaft at the head portion 23, as shown in FIG. 6.

Bristle assembly 30 will now be described in greater detail. The preferred bristle assembly 30 includes a plurality of bristle panels 31 and 32. Each bristle panel advantageously includes a panel frame piece or base 34. Panel bases 34 are the main structural component of each panel. As shown, panel bases 34 are curved crescent shaped pieces which extend across the lower portion of each bristle panel. The bristle panels are also provided with mounting apertures 33 which act as receptacles through which shaft 24 extends when the brush is assembled. The mounting apertures 33 are preferably formed as openings in the panel bases 34.

Bristle panels 31 and 32 each have a plurality of individual bristles 35. The bristles can be arranged in a variety of different configurations, but will preferably be formed as a single row. This arrangement facilitates molding the panels in a strip array and allows sterilization using a sterilizing ultraviolet beam.

As shown, the inner bristle panels 31 use a first type of bristle configuration and the outer bristle panels 32 use a second type of bristle configuration. The preferred bristle configuration of inner bristle panels 31 includes two complementary concave side arrays 39. Concave side arrays 39 extend laterally inward toward a medial line, preferably in an inwardly and upwardly curved sweep relative to the central axis 36 (see FIG. 7). The side arrays 39 are concave when viewed from the front of the brush. Central axis 36 is defined by a centrally located point within apertures 33. The central longitudinal axis of shaft 24 is coincident with mounting aperture central axis 36 when the shaft is installed in the assembled brush.

FIG. 7 also shows that the outer bristle panels 32 advantageously include a bristle configuration which includes three different arrays. A central array 37 and two side arrays 38. The central array 37 has individual bristles which extend upwardly from the panel base portions 34. Overlying central array 37 are convex bristle side arrays 38. Convex side arrays 39 extend laterally inward toward a medial line, preferably in an inwardly and upwardly curved sweep relative to the central axis 36 (see FIG. 7). The side arrays 38 are convex when viewed from the front of the brush. The combination of two different bristle configurations implemented in bristle panels 31 and 32 provides a brushing action which is different from that provided by only one type of bristle configurations. Additional bristle panel types and alternative bristle configurations are also possible.

These bristle arrangements in both types of panels provide a central brushing channel between the opposing side bristles. When combined into the finished brush 20 this arrangement provides a bottom field of bristles and two opposing inwardly directed side fields of bristles. The concave and convex bristles attack particles in different orientation and improve performance. This arrangement brushes the teeth and gums along both lingual and facial surfaces as well as the occlusal surfaces. Distal and mesial surfaces are also engaged as the brush travels over the teeth.

In the preferred embodiment the bristle panels are preferably connected together into one or more concatenated strip arrays. Most preferably the bristle assembly 30 is formed as a single strip connecting all of the bristle panels. This is advantageously done using panel connection webs 41 or other suitable connective links or members. The connective links are preferably integrally molded with the bristle panels to form an integrally formed strip array. This is most preferably accomplished in the form of the integrally molded connective webs 41 which are made from a plastic material which is flexible to allow the strip array to fold and hinge and thereby be pleated, such as shown in FIG. 5. The bristle panel strip is advantageously made from an ethylene vinyl acetate polymer, polyethylene polymer, or other suitable material to provide relatively soft texture when used as a toothbrush. Alternative materials are also possible.

The bristle assembly 30 is held to prevent dislodgement from the end of the shaft by a suitable bristle assembly retainer or anchor. The preferred embodiment illustrated in the Figs. advantageously includes a bristle assembly anchor 50. FIG. 9 shows that bristle assembly anchor 50 is adapted to extend within the interior cavity 26 of the tubular shaft 22 to thereby retain the anchor and adjacent bristle panels 31 and 32 against inadvertent dislodgement. Anchor 50 is provided with a cavity plug or male part 51 which extends within the interior cavity 26 near the head end of shaft 22. The plug is connected to an anchor cap 53. Anchor 50 is most preferably integrally connected to the strip array of bristle panels by an anchor tie connector or hinge 52 (see FIGS. 9 and 4). This preferred construction provides a totally integrated bristle assembly 30 which can conveniently and economically be molded as a single concatenated series of bristle panels 31 and 32, connective webs 41, anchor hinge 52 and anchor 50.

The invention also includes novel methods for constructing brushes. The methods include forming a plurality of bristle panels, such as by molding. The bristle panels preferably are molded in at least one series including a number of individual bristle panels which are integrally connected, such as described hereinabove. Each bristle panel is preferably formed by molding bristles thereon and forming mounting apertures therein.

The methods also advantageously include forming or selecting a suitable shaft. The preferred tubular shaft 24 is described hereinabove. Such a shaft can be formed of extruded polymer material and cut using a shear or other suitable tool to the desired length.

Where a sterilized brush is desired it is appropriate to include the steps of sterilizing the brush 20. This can advantageously be accomplished by separately sterilizing shaft 22 and bristle assembly 30 prior to assembly together. The bristle assembly is molded in a flat strip array and can in this condition be easily sterilized using an ultraviolet beam according to well-known procedures using sufficient intensity and duration to reliably kill microorganisms which may be present. The strip array or other panel configuration and shaft can alternatively be treated by sterilizing the brush in a spacial condition wherein the bristle panels are subject to direct impingement by a bacteriocidal beam. Interior surfaces of the shaft can also be suitably exposed to such a beam for sterilization.

The methods further include mounting the bristle panels upon the selected shaft. This is accomplished by inserting the shaft through receptacles, such as apertures 33, which pass through the bristle panels. The insertion of the shaft is facilitated when a series of connected bristle panels are suitably prepared, such as by first pleating the concatenated series strip array shown in FIG. 4 into the pleated formation shown at the top of FIG. 5. Shaft 24 is then inserted into the apertures in any suitable fashion, such as by sliding the head of the shaft into the apertures. The installed bristle panels form a pleated array of transverse panels in longitudinal juxtaposition upon the shaft.

The novel methods advantageously further comprise the step of anchoring the bristle panels upon the shaft. This is preferably done by securing an integrally formed bristle assembly anchor 50 to the head of the shaft. In the most preferred construction shown and described herein, this securing step is accomplished by inserting an anchor cavity plug 51 within interior cavity 26 of the shaft.

Where a sterilized brush is desired it is possible to assemble the bristle assembly 30 upon the shaft as described above under sterile conditions. This can be done either manually in a sterile chamber having suitable tools or using automated production equipment. It is also appropriate to perform the assembly under ultraviolet light beam to assure sterilization. Packaging into sterilized packages is then accomplished in related packing equipment.

The preferred brush 20 described herein is used as a toothbrush in the typical fashion by applying a dentifrice to the bristles and brushing the teeth. FIG. 10 shows that the pleated bristle assembly 30 can be expanded longitudinally along the tubular shaft 22 to allow the brush to be more easily cleaned after brushing the teeth. Any residual toothpaste or accumulated food debris can thus be easily rinsed away or otherwise dislodged from the bristles by rubbing, preferably under running water. The expanded mode shown in FIG. 10 can also be used as an alternative condition during which beam sterilization can be performed after partial assembly. Compressing the brush into the condition shown in FIG. 6 can then be easily accomplished by automated processing equipment.

In compliance with the statute, the invention has been described in language necessarily limited in its ability to properly convey the conceptual nature of the invention. Because of this inherent limitation of language, it must be understood that the invention is not necessarily limited to the specific features described, since the means herein disclosed comprise merely preferred forms of putting the invention into effect. The invention is, therefore, claimed in any of its forms or modifications within the proper scope of the appended claims appropriately interpreted in accordance with the doctrine of equivalents.

I claim:

1. A brush, comprising:
   a tubular shaft;
   a plurality of bristle panels mounted transversely upon the shaft in relative longitudinal juxtaposition to form a brush head; said bristle panels each having a plurality of flexible bristles thereon; a plurality of said bristle panels being connected together in a strip and pleated onto the shaft;
   an anchor piece which extends into an interior of the tubular shaft and retains the bristle panels upon the shaft.

2. A brush as defined in claim 1 and wherein said anchor piece is integrally formed with said strip of bristle panels.

3. A brush as defined in claim 1 and wherein said anchor piece is a plug.

4. A brush as defined in claim 1 and wherein said anchor piece is a plug having a connected cap.

5. A brush as defined in claim 1 and wherein said anchor piece is a plug integrally formed with said strip of bristle panels.

6. A brush as defined in claim 1 and wherein said plurality of bristle panels have mounting apertures through which the shaft extends.

7. A brush as defined in claim 1 and wherein a plurality of said bristle panels include complementary bristle side arrays which are directed inwardly.

8. A brush as defined in claim 1 and wherein a plurality of said bristle panels include complementary bristle side arrays which are directed inwardly and a bottom bristle array positioned between said side arrays.

9. A brush as defined in claim 1 and wherein a plurality of said bristle panels include bristle arrays which define a bristle channel.

10. A brush as defined in claim 1 and wherein a plurality of said bristle panels include bristle arrays which define a bristle channel; said bristle arrays including at least two different side array configurations which exist at different axial positions along an axis of the brush.

11. A brush as defined in claim 1 wherein said plurality of bristle panels includes at least two different bristle configurations which exist at different axial positions along an axis of the brush.

12. A brush, comprising:
    a tubular shaft;
    a plurality of bristle panels connected together in a strip; said bristle panels having mounting apertures extending therethrough; said bristle panels being mounted upon the shaft with said shaft extending through said mounting apertures;
    an anchor piece connected to said strip and engaged within an interior of said shaft to retain the bristle panels thereon.

13. A brush as defined in claim 12 and wherein said bristle panels are pleated onto the shaft.

14. A brush as defined in claim 12 and further comprising an anchor piece connected to said strip and positioned to engage the shaft and retain the bristle panels thereon.

15. A brush as defined in claim 12 and wherein the shaft is tubular; and further comprising an anchor piece connected to said strip and engaged within an interior of said shaft to retain the bristle panels thereon.

16. A brush as defined in claim 12 and wherein said anchor piece is integrally formed with said strip of bristle panels.

17. A brush as defined in claim 12 and wherein said anchor piece is a plug.

18. A brush as defined in claim 12 and wherein said anchor piece is a plug having a connected cap.

19. A brush as defined in claim 12 and wherein said anchor piece is a plug integrally formed with said strip of bristle panels.

20. A brush as defined in claim 12 and wherein a plurality of said bristle panels include complementary bristle side arrays which are directed inwardly.

21. A brush as defined in claim 12 and wherein a plurality of said bristle panels include complementary bristle side arrays which are directed inwardly and a bottom bristle array positioned between said side arrays.

22. A brush as defined in claim 12 and wherein a plurality of said bristle panels include bristle arrays which define a bristle channel.

23. A brush as defined in claim 12 and wherein a plurality of said bristle panels include bristle arrays which define a bristle channel; said bristle arrays including at least two different side array configurations which exist at different axial positions along an axis of the brush.

24. A brush as defined in claim 12 wherein said plurality of bristle panels includes at least two different bristle configurations which exist at different axial positions along an axis of the brush.

25. A brush, comprising:
   a shaft;
   a plurality of bristle panels connected together in a strip; said bristle panels having mounting apertures extending therethrough; said bristle panels being mounted upon the shaft with said shaft extending through said mounting apertures;
   a plurality of said bristle panels include complementary bristle side arrays which are directed inwardly;
   an anchor piece connected to said strip and engaged within an interior of said shaft to retain the bristle panels thereon.

26. A brush as defined in claim 25 and further comprising a bottom bristle array positioned between said side arrays.

27. A brush as defined in claim 25 and wherein a plurality of said bristle panels include bristle arrays which define a bristle channel; said bristle arrays including at least two different side array configurations which exist at different axial positions along an axis of the brush.

28. A brush as defined in claim 25 wherein said plurality of bristle panels includes at least two different bristle configurations which exist at different axial positions along an axis of the brush.

29. A method for constructing a brush, comprising:
   forming a plurality of bristle panels in a connected series, each bristle panel having a mounting aperture formed therethrough; said connected series of bristle panels further including an anchor connected thereto;
   pleating the connected series of bristle panels;
   mounting the bristle panels upon a shaft by positioning the shaft through the mounting apertures formed in the bristle panels;
   anchoring the pleated series of bristle panels mounted upon the shaft by inserting the anchor into the shaft.

30. A method according to claim 29 and further comprising sterilizing the brush in a spacial condition wherein the bristle panels are subject to direct impingement by a bacteriocidal beam.

* * * * *